(12) United States Patent
Deng et al.

(10) Patent No.: US 8,809,574 B2
(45) Date of Patent: Aug. 19, 2014

(54) METHOD FOR PREPARING ISOCYANATES BY LIQUID-PHASE THERMAL CRACKING

(75) Inventors: Youquan Deng, Lanzhou (CN); Xiaoguang Guo, Lanzhou (CN); Feng Shi, Lanzhou (CN); Qinghua Zhang, Lanzhou (CN); Xiangyuan Ma, Lanzhou (CN); Liujin Lu, Lanzhou (CN); Jian Li, Lanzhou (CN); Xiong Tian, Lanzhou (CN); Yubo Ma, Lanzhou (CN); Jianpeng Shang, Lanzhou (CN); Xinjiang Cui, Lanzhou (CN); Liguo L Wang, Lanzhou (CN); Hongzhe Zhang, Lanzhou (CN)

(73) Assignee: Lanzhou Institute of Chemical Physics, Chinese Academy of Sciences, Lanzhou (CN)

( * ) Notice: Subject to any disclaimer, the term of this patent is extended or adjusted under 35 U.S.C. 154(b) by 609 days.

(21) Appl. No.: 12/637,550

(22) Filed: Dec. 14, 2009

(65) Prior Publication Data
US 2011/0021810 A1    Jan. 27, 2011

(30) Foreign Application Priority Data

Jul. 23, 2009   (CN) .......................... 2009 1 0117379

(51) Int. Cl.
| | | |
|---|---|---|
| *C07C 263/00* | (2006.01) | |
| *B01J 23/843* | (2006.01) | |
| *B01J 31/02* | (2006.01) | |
| *B01J 23/18* | (2006.01) | |
| *B01J 23/10* | (2006.01) | |
| *B01J 23/06* | (2006.01) | |
| *B01J 37/03* | (2006.01) | |
| *C07C 263/04* | (2006.01) | |
| *B01J 23/80* | (2006.01) | |
| *B01J 23/75* | (2006.01) | |
| *B01J 23/02* | (2006.01) | |
| *B01J 23/28* | (2006.01) | |
| *B01J 23/755* | (2006.01) | |
| *B01J 23/745* | (2006.01) | |
| *B01J 23/72* | (2006.01) | |
| *B01J 23/30* | (2006.01) | |

(52) U.S. Cl.
CPC ........... *C07C 263/04* (2013.01); *B01J 23/8437* (2013.01); *B01J 31/0278* (2013.01); *B01J 23/18* (2013.01); *B01J 23/75* (2013.01); *B01J 23/10* (2013.01); *B01J 23/06* (2013.01); *B01J 23/02* (2013.01); *B01J 23/28* (2013.01); *B01J 37/031* (2013.01); *B01J 31/0292* (2013.01); *B01J 31/0288* (2013.01); *B01J 31/0284* (2013.01); *B01J 23/755* (2013.01); *B01J 23/745* (2013.01); *B01J 31/0249* (2013.01); *B01J 23/72* (2013.01); *B01J 23/30* (2013.01); *B01J 23/80* (2013.01)
USPC ........................................................ 560/338

(58) Field of Classification Search
CPC ........................... C07C 263/04; C07C 263/10
See application file for complete search history.

(56) References Cited

U.S. PATENT DOCUMENTS

| | | | | |
|---|---|---|---|---|
| 3,202,618 A | * | 8/1965 | Jaffe ............................. | 502/308 |
| 3,962,302 A | | 6/1976 | Rosenthal et al. | |
| 3,993,584 A | * | 11/1976 | Owen et al. .................... | 252/383 |
| 4,294,774 A | | 10/1981 | Henson et al. | |
| 4,349,484 A | | 9/1982 | Merger et al. | |
| 4,388,246 A | * | 6/1983 | Sundermann et al. ........ | 560/345 |
| 2009/0112017 A1 | * | 4/2009 | Sesing et al. .................. | 560/347 |

FOREIGN PATENT DOCUMENTS

| | | | |
|---|---|---|---|
| CN | 101195590 A | | 6/2008 |
| WO | WO 2006048171 | * | 5/2006 |

OTHER PUBLICATIONS

Derwent Abstract of CN 101195590, Deng, Y., Preparation of 1,6-hexamethylene diisocyanate by liquid phase thermal cracking hexamethylene diamido methyl formate comprises reacting hexamethylene diamido methyl formate and ion liquid solvent under catalysis, Jun. 11, 2008.*
English Translation of Deng et al. CN 101195590.*
Deng, "Ionic Liquid-Property, Preparation and Application," China Petrochemical Press, 2006 (with Abstract).

* cited by examiner

*Primary Examiner* — Rosalynd Keys
*Assistant Examiner* — Jennifer C Sawyer
(74) *Attorney, Agent, or Firm* — Oliff PLC

(57) ABSTRACT

The present invention discloses a method for preparing isocyanates by liquid-phase catalytic thermal cracking. In this method, in a reaction-rectification thermal cracking reactor, using a catalyst composition comprising a superfine powder metal oxide catalyst and an ionic liquid, an alkyl or aryl dialkylurethane, or multialkylurethane being a reactant is liquid-phase thermal cracked for a reaction time of 0.5-3 h under a reaction temperature of 160-220° C. and an absolute pressure of 1000-8000 Pa so as to prepare the corresponding isocyanate. The invention has the characteristics of low thermal cracking temperature, high yield of target products, relatively simple reaction apparatus and good universality for substrates (the yields of HDI, MDI, TDI, HMDI, NDI and IPDI or the like are all>85%) and the like.

12 Claims, No Drawings

METHOD FOR PREPARING ISOCYANATES BY LIQUID-PHASE THERMAL CRACKING

FIELD OF THE INVENTION

The present invention relates to a method for preparing isocyanates by liquid-phase catalytic thermal cracking.

BACKGROUND OF THE INVENTION

Being a kind of important intermediates in organic reactions, isocyanates have a very wide application in industry, agriculture, medication and the like. This kind of compounds is broadly utilized in synthesizes of polyisocyanates, polyurethanes, polyureas, polymeric adhesives, insecticides, herbicides and the like.

Both aliphatic diisocyanates and aromatic diisocyanates are very useful industrial raw materials. For example, as an important raw material for preparing polyurethanes, aromatic 4,4-diphenylmethane diisocyanate (MDI) is widely applied in the preparations of microporous elastomers, thermoplastic elastomers, casting elastomers, leatheroids, synthetic leathers, adhesives, coatings, sealing agents and the like. As an industrial raw material, 2,4/2,6-toluene diisocyanate (TDI) is widely applied in the productions of polyurethane foaming plastics, polyurethane elastomers and millable elastomers, polyurethane coatings, polyurethane adhesives, polyurethane water-proof materials, detergents, thickening agent, antioxidants and the like. As a raw material for advanced polyurethanes, 1,5-naphthalene diisocyanate (NDI) can be used to manufacture polyurethane elastomers with high elasticity and high hardness. NDI polyurethane elastomers are widely used for automobile shock absorbers, forklift wheel bearings, printing and weaving rubber rollers, rubber scrapers, bridge-building buffers, entertainments or the like.

After being exposed outside, aliphatic and alicyclic diisocyanates do not get yellow, and therefore, they are also referred to as non-yellowing isocyanates. For example, 1,6-hexane diisocyanate (HDI) is mainly used for advanced coatings and refinishing paints for automobiles, OEM coatings and refinishing paints for airplanes, anticorrosive coatings, wood furniture paints, paints for enamel-insulated wires, refinishing paints for trains, polyurethane sizing agents with good light stability and rocket propellant additives or the like. 3-isocyanatomethyl-3,5,5-trimethylcyclohexyl isocyanate (isophorone diisocyanate) (IPDI) is mainly used to prepare aliphatic polyisocyanate derivatives, such as, polymers, trimers, adducts, which are used for excellent weather-proof polyurethane coatings, as well as weaving, PU leathers and many plastic products widely. 4,4-dicyclohexylmethane diisocyanate (HMDI) is mainly used for polyurethane foaming plastics, polyurethane elastomers and millable elastomers, polyurethane coatings, polyurethane adhesives, anticorrosive coatings, wood furniture paints or the like.

At present, isocyanates are mainly prepared by the reaction of the corresponding amine compounds and phosgene. Phosgene is a virulent compound, and additionally, a great deal of strong corrosive hydrogen chloride will be produced during the reaction. Therefore, it will result in apparatus corrosion and phosgene leakage which cause environment pollution and personnel injury.

With the increasing aggravation of environment pollution in the world, all countries implement continuously environment protecting measures in a manner of lows by force to control the usage and discharge of the poisonous harmful substances. The research and development for a clean productive technique of isocyanate chemicals by non-phosgene preparation has become an attractive area for the scientific institutions and chemical factories. The preparation of isocyanate chemicals by non-phosgene method is of benefit to the environment protection, and additionally, as there is no chlorine in the production medium, products with higher quality can be produced.

During the past 20 years or more, in order to find a safe, cheap, environment-friendly synthetic method for isocyanates, the people have carried out many researching work and found several routes for prepare isocyanates by non-phosgene method. In all of these, a route with the most industrialized perspective is a method of performing a carbonylation reaction by using an organic amine as raw material and taking dialkyl carbonate or small molecule alkyl urethane as carbonylation agent to synthesize the corresponding urethane, and then thermal cracking the urethane to obtain the corresponding isocyanate and alcohol.

The processing reaction condition for synthesizing the corresponding urethane from the organic amine and the carbonylation agent is relatively mild and easy to be realized. However, the thermal cracking process relates to higher temperature and is generally carried out under negative pressure. Additionally, isocyanates have relatively active chemical property and are easy to perform side reactions. Therefore, it is a critical and difficult process in the route for preparing isocyanates by a non-phosgene synthesis. The thermal cracking process is often attended by many side reactions, which will not only reduce the yield, but also block the reactors and other apparatuses. At the same time, as the vapor-phase thermal cracking has high reaction temperature (350-450° C.), many side reactions and low yield, the value of industrial application thereof is reduced. However, the liquid-phase thermal cracking with lower reaction temperature (200-350° C.) and higher yield has become a researching focus for numerous scientists gradually.

In U.S. Pat. No. 3,962,302, TDI was synthesized by thermal cracking toluene diethylurethane under nitrogen atmosphere at 250° C. in the case of taking cetane as solvent. The yield was 83.4%. In U.S. Pat. No. 4,294,774, Henson et al. prepared MDI with a yield of 46% when N,N-dimethylaniline was used as solvent and catalyst. In U.S. Pat. No. 4,349,484, Merger et al. prepared MDI with a yield of 76.5% by decomposing diphenylmethane dimethylurethane at high pressure and high temperature (310° C.), wherein decylbenzene was taken as solvent and filling zinc scraps were taken as catalyst. The above reactions have the following disadvantages of: (1) the reaction performed in the kettle reactor has a low yield; (2) under the condition of relatively high temperature and negative pressure, the high boiling solvents have the problems of decomposition, loss and the like; (3) as the alcohols produced cannot be separated in time, the alcohols tend to react with the isocyanates; (4) as isocyanates have active chemical properties, they tend to perform the side reactions of polymerization and the like.

The known researching results indicate that during the process of liquid-phase thermal cracking, the choice of solvents is critical in addition to the choice of appropriate catalysts and reactors. However, as the media in the thermal cracking process, the existing high boiling molecule type solvents have some formidable limitations.

In the previous researching work of the inventors (Youquan Deng, Xiaoguang Guo, Chinese invention patent application No.: 200610105297.3), 1,6-hexane diisocyanate was prepared by thermal cracking hexamethylene dimethylurethane in liquid phase in the case of using a supported solid catalyst (the catalyst was small spheres with a diameter of 2-5 millimeters) and an ionic liquid multiphase catalytic system. Comparing with the previous thermal cracking methods based on high boiling point molecule type solvents, the thermal cracking method based on ionic liquids have the advantages of less solvent addition, lower temperature of thermal cracking reaction, less by-products, higher thermal stability of ionic liquids, and reutilization and the like. However, there are also some disadvantages for above mentioned supported solid catalyst+ionic liquid multiphase catalytic system. For example, in the case of using a fixed bed reactor filled with a supported metal oxide solid catalyst, the ionic liquid containing reactants has relatively large flowing resistance and is difficult to be circulated, and therefore, the reaction efficiency thereof is lower and the reaction device is complex relatively. The amount of the supported catalyst charged is relatively large and the active components are easy to be lost, and therefore, the life of the catalyst is shorter which goes against the industrial application, and the universality of the catalyst system is lower.

SUMMARY OF THE INVENTION

An aim of the invention is to disclose a method for preparing isocyanates by liquid-phase thermal cracking.

Aiming at the problems described in the background, the present invention made improvements for the supported solid catalyst and reaction system. That is, the previous 2-5 mm diameter small sphere supported metal oxide catalyst is substituted by a superfine powder metal oxide or composite metal oxide catalyst, and the previous multiphase thermal cracking system is substituted by a liquid-phase thermal cracking system. These improvements completely solve the problem of the active component loss of the catalyst and the relatively large flowing resistance of the reactants and ionic liquid among layers in the bed, reduce the loading amount of the catalyst, and at the same time, increase the reaction efficiency. By adjusting the compositions of the superfine powder metal oxide or composite metal oxide catalyst, the universality for the precursors of isocyanates, that is, alkyl or aryl dialkylurethane, is increased greatly, and therefore, this method has more value of industrial application.

The invention describes a method for preparing isocyanate by a liquid-phase catalytic thermal cracking of alkyl or aryl dialkylurethane in the presence of a catalyst composition comprising a superfine powder metal oxide catalyst and an ionic liquid.

A method for preparing isocyanates by liquid-phase thermal cracking, characterized in that in a reaction-rectification thermal cracking reactor, using a catalyst composition comprising a superfine powder metal oxide catalyst and an ionic liquid, an alkyl or aryl dialkylurethane, or multialkylurethane being a reactant is liquid-phase thermal cracked for a reaction time of 0.5-3 h under a reaction temperature of 160-220° C. and an absolute pressure of 1000-8000 Pa so as to prepare the corresponding isocyanate.

The superfine powder metal oxide catalyst as described in the invention is a metal oxide or a composite of metal oxides, which is at least one, preferably one, two or three, selected from the group consisting of nickel oxide, titanium oxide, zirconium oxide, copper oxide, molybdenum oxide, iron oxide, tungsten oxide, lanthanum oxide, cerium oxide, cobalt oxide, zinc oxide, calcium oxide, yttrium oxide and bismuth oxide.

The method for preparing the superfine powder metal oxide catalyst as described in the invention is a coprecipitation or sol-gel process. In the coprecipitation process, the preparation of a coprecipitation catalyst can be realized by adjusting the pH value in this process of the aqueous solution to be 5-8 via the addition of acid or base; in the sol-gel process, the preparation of a sol-gel catalyst can be realized by adjusting the gelling process via the addition of concentrated nitric acid or concentrated hydrochloric acid and citric acid.

In the preparation method of the superfine powder metal oxide catalyst as described in the invention, the calcination temperature for the catalyst precursors is preferably 300-700° C.; and the calcination time is preferably 2-10 hours.

In some embodiments, the superfine powder metal oxide catalyst as described in the invention is a two component (A/B) metal oxide catalyst having a mass ratio (A/B) of 50:1-1:50.

In some embodiments, the superfine powder metal oxide catalyst as described in the invention is a three component (A/B/C) metal oxide catalyst, wherein A comprises 10 wt %, B comprises 10 wt %, and the rest is C, based on the total weight of the superfine powder metal oxide catalyst.

Preferably, the particle diameter of the superfine powder metal oxide catalyst as described in the invention is 0.5-10 micrometers.

For the ionic liquid as described in the invention, preferably, the cation thereof may be represented by one selected from the following 4 structural formulas:

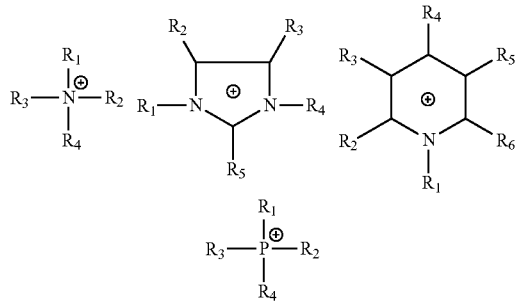

wherein $R_1, R_2, R_3, R_4, R_5, R_6$ each independently represents branched or substituted alkyl groups with a carbon number between 1 and 15.

For the ionic liquid as described in the invention, preferably, the anion thereof may be one selected from the group consisting of $NO_3^-$, $PF_6^-$, $ClO_4^-$, $CH_3PhSO_3^-$, $C(CN)_3^-$, $N(CN)_2^-$, $BF_2(CF_2)_nCF_3^-$ (n=0-10), $PF_3(CF_2)_nCF_3^-$ (n=0-10), $N(CF_3SO_2)_2^-$, $SCN^-$, $SeCN^-$, $RSO_3^-$ (R has a carbon number of 0-10), $RSO_4^-$ (R has a carbon number of 0-10), $M_nY_x$ (M=Al, Zn, Fe, Sn, X=Cl, Br, I, n=1-2, x=2-7), $RCOO^-$ (R has a carbon number of 0-18), $BF_4^-$, $H_2PO_4^-$, $CF_3COO^-$, $CF_3SO_3^-$, $SbF_6^-$, $AsF_6^-$, $EtSO_4^-$, $MeSO_4^-$, $Cl^-$, $Br^-$ and $I^-$.

The preparation method and property of the ionic liquid as described in the invention can be seen in Youquan Deng, "Ionic Liquids-property, preparation and application [M]", China Petrochemical Press, 2006, 7.

In the catalyst composition as described in the invention, preferably, the mass ratio of the superfine powder metal oxide catalyst to the ionic liquid is from 1:300 to 1:15000.

In some embodiments, the alkyl or aryl dialkylurethane as described in the invention (preferably, wherein the diallyl- is the corresponding dimethyl-, diethyl- or dibutyl-) is selected from the group consisting of hexamethylene 1,6-dialkylurethane, dicyclohexylmethane-4,4'-dialkylurethane, isophorone dialkylurethane, p-cyclohexyldialkylurethane, diphenylmethane-4,4'-dialkylurethane, bis(2-tolyl)methane-4,4'-dialkylurethane, toluene-2,4-dialkylurethane, toluene-2,6- dialkylurethane, benzene-1,4-dialkylurethane and naphthalene-1,5-dialylurethane.

In some embodiments of the method as described in the invention, the mass ratio of the reactant alkyl or aryl dialkylurethane to the ionic liquid is from 1:1 to 1:50.

In some embodiments of the method for preparing isocyanates by liquid-phase catalytic thermal cracking, the cracking is carried out at a preferable reaction temperature of 160-220° C., a preferable absolute pressure of 1000-8000 Pa and a preferable reaction time of 0.5-3 h.

According to some embodiments, the liquid-phase catalytic thermal cracking is carried out using reaction-rectification technique, that is, reaction and product separation can be carried out concurrently in the same reaction system.

According to some embodiments, the method for preparing isocyanates by liquid-phase catalytic thermal cracking in the invention can be carried out according to the following processes. Into a reaction-rectification thermal cracking reactor, a superfine powder metal oxide catalyst, an ionic liquid and is an alkyl or aryl dialkylurethane are added. Then, a thermal cracking is performed by adjusting the reaction temperature to be 160-220° C. and the degree of vacuum to be 1000-8000 Pa. Because of the relatively large boiling point differences in ionic liquid-metal oxide catalyst system, the desired isocyanate and the alcohol byproduct, which were produced during the thermal cracking, the separation among them can be realized conveniently. That is, the isocyanate is collected into a pre-collecting device with a condensing temperature of 0° C.-10° C., and the alcohol is collected into a post-collecting device with a condensing temperature of about −10° C. to −30° C. Finally, the mixture in the condensing device is analyzed qualitatively and quantitatively by gas chromatography (GC), gas chromatography-mass spectrum (GC-MS), high performance liquid chromatography (HPLC). An isocyanate with certain purity is obtained by subjecting the mixture in the pre-collecting device to rectification. A separation yield is calculated by weighing. The residual small amount of urethanes and intermediates through the rectification separation can be recovered and reused.

Comparing with the existing technique using a high boiling solvent system, the superfine powder metal oxide-ionic liquid liquid-phase catalytic system used in the invention has the following advantages:
1. The addition of solvent (ionic liquid) is less;
2. The ionic liquid is almost nonvolatile, which can help to separate the product and reduce the ionic liquid loss.
3. Due to the special ionic environment of ionic liquid, it is not necessary to add an antipolymerizer anymore;
4. The reaction temperature of thermal cracking is decreased so that the production of a byproduct is reduced obviously;
5. Due to the high thermal stability of ionic liquid, it can be reused for many times.

Comparing with the existing technique for preparing hexamethylene-1,6-diisocyanate by thermal cracking hexamethylene-1,6-dimethylurethane using supported solid catalyst-ionic liquid (Youquan Deng, Xiaoguang Guo, et al., Chinese Invention Patent Application No.: 200610105297.3), it further has the following advantages:
1. There is no loss of the supported solid catalyst active components;
2. The amount of the superfine powder metal oxide catalyst charged is reduced;
3. The flowing resistance of the reactants and ionic liquid is reduced greatly;
4. The reaction efficiency is increased and at the same time, the reaction apparatus is simplified;
5. The method can be applied to various alkyl or aryl dialkylurethane and has more value of industrial application.

DETAILED DESCRIPTION OF THE PREFERRED EMBODIMENTS

The preparation of a superfine powder metal oxide catalyst in a catalyst composition Example 1

Under a condition of 65° C. water bath and magnetic stirring, 50 g of $Zn(NO_3)_2 \cdot 6H_2O$ was dissolved into 100 mL distilled water. After complete dissolution, 20 g of concentrated nitric acid and 55 g of citric acid were added and stirred until gelatination occurred. After aging for 24 h, the mixture was washed with distilled water until the pH value approached to 7, then dried at 80° C. under vacuum for 5 hours, and finally, calcined in a muffle furnace at 400° C. for 6 hours to obtain a catalyst A. The catalyst A, i.e. the superfine powders of ZnO, comprised 100 wt % of ZnO.

Example 2

Under a condition of magnetic stirring or ultrasonic stirring, 79.7 g of $La(NO_3)_3 \cdot 6H_2O$ and 5.48 g of $Zn(NO_3)_2 \cdot 6H_2O$ was dissolved into 240 mL distilled water. After complete dissolution, the solution was added dropwise with 1 M $NaCO_3$ aqueous solution until the precipitation was completed and the pH value of the supernatant was 7. After aging for 1-2 hours, a precipitate was filtrated and dried in a drying oven at 120° C. for about 20 hours, and then calcined in a muffle furnace at 500° C. for 6 hours. After being cooled to room temperature, it was ground in an agate mortar for 30 min to obtain a catalyst B. The catalyst B, i.e. the superfine powders of $ZnO/La_2O_3$, comprised 96 wt % of $La_2O_3$ and 4 wt % of ZnO.

Example 3

Under a condition of magnetic stirring or ultrasonic stirring, 79.7 g of $La(NO_3)_3 \cdot 6H_2O$, 5.48 g of $Zn(NO_3)_2 \cdot 6H_2O$ and 3.3 g of $Cd(NO_3)_2 \cdot 4H_2O$ was dissolved into 240 mL distilled water. After complete dissolution, the solution was added dropwise with 1 M $NaCO_3$ aqueous solution until the precipitation was completed and the pH value of the supernatant was 7. After aging for 1-2 hours, a precipitate was filtrated and dried in a drying oven at 120° C. for about 20 hours, and then calcined in a muffle furnace at 600° C. for 6 hours. After being cooled to room temperature, it was ground in an agate mortar for 30 min to obtain a catalyst C. The catalyst C, i.e. the superfine powders of $ZnO-CdO/La_2O_3$, comprised 92 wt % of $La_2O_3$, 4 wt % of ZnO and 4 wt % of CdO.

Example 4

Under a condition of magnetic stirring or ultrasonic stirring, 3.0 g of $Zn(NO_3)_2 \cdot 6H_2O$ and 50.5 g of $Fe(NO_3)_3 \cdot 9H_2O$ was dissolved into 100 mL distilled water. Then, the above solution was added dropwise with 0.5 M $NaCO_3$ aqueous solution until the precipitation was completed and the pH value of the supernatant was 7. After aging for 1-2 hours, a precipitate was filtrated and dried in a drying oven at 120° C. for about 20 hours, and then calcined in a muffle furnace at 550° C. for 6 hours. After being cooled to room temperature, it was ground in an agate mortar for 30 min to obtain a catalyst D. The catalyst D, i.e. the superfine powders of $ZnO/Fe_2O_3$, comprised 5 wt % of ZnO and 95 wt % of $Fe_2O_3$.

Example 5

Under a condition of magnetic stirring or ultrasonic stirring, 2.08 g of $Bi(NO_3)_2 \cdot 6H_2O$ and 50.5 g of $Fe(NO_3)_3 \cdot 9H_2O$ was dissolved into 100 mL nitric acid solution (pH=3-4). Then, the above solution was added dropwise with 0.5 M $NaCO_3$ aqueous solution until the precipitation was completed and the pH value of the supernatant was 7. After aging for 1-2 hours, a precipitate was filtrated and dried in a drying oven at 100° C. for about 15 hours, and then calcined in a muffle furnace at 500° C. for 4 hours so as to obtain $Bi_2O_3/Fe_2O_3$. Then it was reduced for 1.5 h at 400° C. under 30 mL/min $H_2$ atmosphere. After being cooled to room temperature, it was ground in an agate mortar for 30 min to obtain a catalyst E. The catalyst E, i.e. the superfine powders of $Bi_2O_3/Fe_3O_4$, comprised 5 wt % of $Bi_2O_3$ and 95 wt % of $Fe_3O_4$.

The Preparation of the Ionic Liquid Catalyst and Medium

The preparation method and property of the used ionic liquid can be seen in Youquan Deng, "Ionic Liquids-property, preparation and application [M]", China Petrochemical Press, 2006, 7.

Preparation of Isocyanates by Liquid-Phase Catalytic Thermal Cracking (the Synthesis of Common Diisocyanates is Mainly Presented)

The quantitative analysis of a diisocyanate could utilize Agilent 1790 GC with a 30 m×0.25 mm×0.33 µm capillary (FID detector). The diisocyanate was quantified by external standard method. The quantitative analysis of an alkyl or aryl diurethane could utilize Agilent 1200 HPLC, wherein the Agilent 1200 HPLC had a DDA monitor, the mobile phase thereof was acetonitrile:tetrahydrofuran=55%:45%, and the chromatographic column thereof was Waters XTerra RP C18 (250×4.6 mm, 5 µm). The qualitative analysis of the reaction could utilize HP 6890/5973 GC-MS which has a 30 m×0.25 mm×0.33 µm capillary and a chemstation with a NIST optical spectrum database.

Example 6

In to a thermal cracking device, 500 mL of N-trimethyl-butyltetrafluoroboric acid ionic liquid ($[N_{1114}]BF_4$) and 0.5 g of supported metal oxide solid catalyst A were added. At 200° C., under an absolute pressure of 6500 Pa and a stirring rotation speed of 400 rounds/min, 200 g of diphenylmethane-4,4-dimethylurethane was further added. After reacting for 0.5 h, diphenylmethane diisocyanate (MDI) and methanol were collected in the pre-(about 0° C.), post-(about −20° C.) collecting devices, respectively. The reaction was continued for 2 hours at 200° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing diphenylmethane-4-isocyanate-4-methylurethane (monoisocyanate), diphenylmethane-4,4'-dimethylurethane and MDI. The mixing liquid was subjected to chromatography analysis. The measured MDI had a purity of 93% and a chromatography yield of 88%. Then the mixing liquid was subjected to rectification. The isolated MDI yield was 84% and the purity was 98%. The residual product after rectification was subjected to the next thermal cracking for circulation in turn. The ionic liquid could be reused for several times.

Example 7

In to a thermal cracking device, 400 g of tetrabutylphosphine trifluoromethanesulfonimide ionic liquid ($[P_{4444}]NTf_2$) and 0.2 g of supported metal oxide solid catalyst E were added. At 180° C., under an absolute pressure of 6500 Pa and a stirring rotation speed of 400 rounds/min, 220 g of diphenylmethane-4,4-dibutylurethane was further added. After reacting for 0.5 h, diphenylmethane diisocyanate (MDI) and butanol were collected in the pre-(about 0° C.), post-(about −20° C.) collecting devices, respectively. The reaction was continued for 2 hours at 180° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing diphenylmethane-4-isocyanate-4-butylurethane (monoisocyanate), diphenylmethane-4,4-dibutylurethane and MDI. The mixing liquid was subjected to chromatography analysis. The measured MDI had a purity of 88% and a chromatography yield of 83%. Then the mixing liquid was subjected to rectification. The isolated MDI yield was 79%. The residual product after rectification was subjected to the next thermal cracking for circulation in turn. The ionic liquid could be reused for several times.

Example 8

In to a thermal cracking device, 500 mL of 1-methyl-3-butylimidazole tetrafluoroboric acid ionic liquid ($[BMIm]BF_4$) and 0.6 g of supported metal oxide solid catalyst B were added. At 200° C., under an absolute pressure of 5000 Pa and a stirring rotation speed of 600 rounds/min, 225 g of naphthalene-1,5-dimethylurethane was further added. After reacting for 0.5 h, 1,5-naphthalene diisocyanate (NDI) and methanol were collected in the pre-(about 0° C.), post-(about −20° C.) collecting devices, respectively. The reaction was continued for 1.5 hours at 200° C. under a degree of vacuum of 5000 Pa. Then, the temperature was turned to 240° C. under the same degree of vacuum for 10 min. All of the products, raw materials and intermediates in the thermal cracking device were collected into the pre-collecting device to obtain a mixture containing 1,5-naphthalene-isocyanate-methylurethane (monoisocyanate), naphthalene-1,5-dimethylurethane and NDI. The mixing liquid was subjected to chromatography analysis. The measured NDI had a purity of 90% and a NDI chromatography yield of 89%. Then the mixing liquid was subjected to rectification. The isolated NDI yield was 85%. The residual product after rectification was subjected to the next thermal cracking for circulation in turn. The ionic liquid could be reused for several times.

Example 9

In to a thermal cracking device, 500 mL of 1-methyl-3-ethylimidazole tetrafluoroboric acid ionic liquid ($[EMIm]BF_4$) and 0.8 g of supported metal oxide solid catalyst C were added. At 190° C., under an absolute pressure of 5000 Pa and a stirring rotation speed of 600 rounds/min, 210 g of naphthalene-1,5-diethylurethane was further added. After reacting for 0.5 h, 1,5-naphthalene diisocyanate (NDI) and ethanol were collected in the pre-(about 0° C.), post-(about −20° C.) collecting devices, respectively. The reaction was continued for 1.5 hours at 190° C. under a degree of vacuum of 5000 Pa. Then, the temperature was turned to 240° C. under the same degree of vacuum for 10 min. All of the products, raw materials and intermediates in the thermal cracking device were collected into the pre-collecting device to obtain a mixture containing 1,5-naphthalene-isocyanate-ethylurethane (monoisocyanate), naphthalene-1,5-diethylurethane and NDI. The mixing liquid was subjected to chromatography analysis. The measured NDI had a purity of 90% and a NDI chromatography yield of 89%. Then the mixing liquid was subjected to rectification. The isolated NDI yield was 85%. The residual product after rectification was subjected to the next thermal cracking for circulation in turn. The ionic liquid could be reused for several times.

Example 10

In to a thermal cracking device, 500 mL of 1,2-dimethyl-4-ethylimidazole perchloric acid ionic liquid ([EMMIm]ClO$_4$) and 0.5 g of supported metal oxide solid catalyst E were added. At 190° C., under an absolute pressure of 5000 Pa and a stirring rotation speed of 600 rounds/min, 235 g of naphthalene-1,5-dibutylurethane was further added. After reacting for 0.5 h, 1,5-naphthalene diisocyanate (NDI) and butanol were collected in the pre-(about 0° C.), post-(about −20° C.) collecting devices, respectively. The reaction was continued for 1.5 hours at 190° C. under a degree of vacuum of 5000 Pa. Then, the temperature was turned to 240° C. under the same degree of vacuum for 10 min. All of the products, raw materials and intermediates in the thermal cracking device were collected into the pre-collecting device to obtain a mixture containing 1,5-naphthalene-isocyanate-butylurethane (monoisocyanate), naphthalene-1,5-dibutylurethane and NDI. The mixing liquid was subjected to chromatography analysis. The measured NDI had a purity of 93% and a NDI chromatography yield of 95%. Then the mixing liquid was subjected to rectification. The isolated NDI yield was 91%. The residual product after rectification was subjected to the next thermal cracking for circulation in turn. The ionic liquid could be reused for several times.

Example 11

In to a thermal cracking device, 540 g of 1-methyl-3-ethylimidazole hexafluorophosphoric acid ionic liquid ([EMIm]PF$_6$) and 0.4 g of supported metal oxide solid catalyst D were added. At 200° C., under an absolute pressure of 6500 Pa and a stirring rotation speed of 450 rounds/min, 225 g of toluene-2,4-dimethylurethane was further added. After reacting for 0.5 h, 2,4-toluene diisocyanate (TDI) and methanol were collected in the pre-(about 0° C.), post-(about 20° C.) collecting devices, respectively. The reaction was continued for 1.5 hours at 200° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing toluene-4-isocyanate-2-methylurethane (monoisocyanate), toluene-2,4-dimethylurethane and TDI. The mixing liquid was subjected to chromatography analysis. The measured TDI had a purity of 90% and a TDI chromatography yield of 90%. Then the mixing liquid was subjected to rectification. The isolated TDI yield was 86%. The residual product after rectification was subjected to the next thermal cracking for circulation in turn. The ionic liquid could be reused for several times.

Example 12

In to a thermal cracking device, 550 g of 1,2-dimethyl-3-ethylimidazole hexafluorophosphoric acid ionic liquid ([EMMIm]PF$_6$) and 1 g of supported metal oxide solid catalyst C were added. At 190° C., under an absolute pressure of 6500 Pa and a stirring rotation speed of 500 rounds/min, 220 g of toluene-2,4-diethylurethane was further added. After reacting for 0.5 h, 2,4-toluene diisocyanate (TDI) and ethanol were collected in the pre-(about 0° C.), post-(about −20° C.) collecting devices, respectively. The reaction was continued for 1.5 hours at 190° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing toluene-4-isocyanate-2-ethylurethane (monoisocyanate), toluene-2,4-diethylurethane and TDI. The mixing liquid was subjected to chromatography analysis. The measured TDI had a purity of 86% and a TDI chromatography yield of 89%. Then the mixing liquid was subjected to rectification. The isolated TDI yield was 85%. The residual product after rectification was subjected to the next thermal cracking for circulation in turn. The ionic liquid could be reused for several times.

Example 13

In to a thermal cracking device, 550 g of 1,2-dimethyl-3-ethylimidazole trifluoromethanesulfonimide ionic liquid ([EMMIm]NTf$_2$) and 0.5 g of supported metal oxide solid catalyst E were added. The rest condition and process were the same as that of Example 12. The mixing liquid was subjected to chromatography analysis. The measured TDI had a purity of 94% and a TDI chromatography yield of 95%. Then the mixing liquid was subjected to rectification. The isolated TDI yield was 91%. The residual product after rectification was subjected to the next thermal cracking for circulation in turn. The ionic liquid could be reused for several times.

Example 14

In to a thermal cracking device, 550 g of 1,2-dimethyl-3-ethylimidazole perchlorate ionic liquid ([EMMIm]ClO$_4$) and 0.5 g of supported metal oxide solid catalyst E were added. At 180° C., under an absolute pressure of 6500 Pa and a stirring rotation speed of 550 rounds/min, 230 g of toluene-2,4-dibutylurethane was further added. After reacting for 0.5 h, 2,4-toluene diisocyanate (TDI) and butanol were collected in the pre-(about 0° C.), post-(about −20° C.) collecting devices, respectively. The reaction was continued for 1.5 hours at 180° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing toluene-4-isocyanate-2-butylurethane (monoisocyanate), toluene-2,4-dibutylurethane and TDI. The mixing liquid was subjected to chromatography analysis. The measured TDI had a purity of 95% and a TDI chromatography yield of 96%. Then the mixing liquid was subjected to rectification. The isolated NDI yield was 92%. The residual product after rectification was subjected to the next thermal cracking for circulation in turn. The ionic liquid could be reused for several times.

Example 15

In to a thermal cracking device, 500 mL of 1-methyl-3-butylimidazole trifluoromethanesulfonic acid ionic liquid ([BMIm]CF$_3$SO$_3$) and 0.8 g of supported metal oxide solid catalyst A were added. At 200° C., under an absolute pressure of 6500 Pa and a stirring rotation speed of 450 rounds/min, 220 g of dicyclohexylmethane-4,4-dimethylurethane was further added, After reacting for 0.5 h, dicyclohexylmethane-4,4-diisocyanate (HMDI) and methanol were collected in the pre-(about 0° C.), post-(about −20° C.) collecting devices, respectively. The reaction was continued for 1 hours at 200° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing dicyclohexylmethane-4-isocyanate-4-methylurethane (monoisocyanate), dicyclohexylmethane-4,4-dimethylurethane and HMDI. The mixing liquid was subjected to chromatography analysis. The measured HMDI had a purity of 88% and a HMDI chromatography yield of 85%. Then the mixing liquid was subjected to rectification. The isolated HMDI yield was 81%. The residual product after rectification was subjected to the next thermal cracking for circulation in turn. The ionic liquid could be reused for several times.

Example 16

In to a thermal cracking device, 500 g of 1,2-dimethyl-3-ethylimidazole nitrate ionic liquid ([EMMIm]NO$_3$) and 1 g of supported metal oxide solid catalyst E were added. At 200° C., under an absolute pressure of 6500 Pa and a stirring rotation speed of 400 rounds/min, 240 g of dicyclohexylmethane-4,4-diethylurethane was further added. After reacting for 0.5 h, dicyclohexylmethane-4,4-diisocyanate (HMDI) and ethanol were collected in the pre-(about 0° C.), post-(about −20° C.) collecting devices, respectively. The reaction was continued for 1 hours at 200° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing dicyclohexylmethane-4-isocyanate-4-ethylurethane (monoisocyanate), dicyclohexylmethane-4,4-diethylurethane and HMDI. The mixing liquid was subjected to chromatography analysis. The measured HMDI had a purity of 92% and a HMDI chromatography yield of 95%. Then the mixing liquid was subjected to rectification. The isolated HMDI yield was 91%. The residual product after rectification was subjected to the next thermal cracking for circulation in turn. The ionic liquid could be reused for several times.

Example 17

In to a thermal cracking device, 500 g of 1,2-dimethyl-3-ethylimidazole hexafluorophosphoric acid ionic liquid ([EMMIm]PF$_6$) and 0.8 g of supported metal oxide solid catalyst E were added. At 190° C., under an absolute pressure of 6500 Pa and a stirring rotation speed of 500 rounds/min, 240 g of dicyclohexylmethane-4,4-dibutylurethane was further added. After reacting for 0.5 h, dicyclohexylmethane-4,4-diisocyanate (HMDI) and butanol were collected in the pre-(about 0° C.), post-(about −20° C.) collecting devices, respectively. The reaction was continued for 1 hours at 200° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing bicyclohexylmethane-4-isocyanate-4-butylurethane (monoisocyanate), dicyclohexylmethane-4,4-dibutylurethane and HMDI. The mixing liquid was subjected to chromatography analysis. The measured HMDI had a purity of 94% and a HMDI chromatography yield of 92%. Then the mixing liquid was subjected to rectification. The isolated HMDI yield was 88%. The residual product after rectification was subjected to the next thermal cracking for circulation in turn. The ionic liquid could be reused for several times.

Example 18

In to a thermal cracking device, 500 mL of 1,2-dimethyl-3-ethylimidazole tetrafluoroboric acid ionic liquid ([EMMIm]BF$_4$) and 0.4 g of supported metal oxide solid catalyst D were added. At 200° C., under an absolute pressure of 6500 Pa and a stirring rotation speed of 450 rounds/min, 220 g of 3-methoxycarbonylaminomethyl-3,5,5-trimethyl-1-methoxycarbonylaminocyclohexane (isophorone dimethylurethane) was further added. After reacting for 0.5 h, isophorone diisocyanate (IPDI) and methanol were collected in the pre-(about 0° C.), post-(about −20° C.) collecting devices, respectively. The reaction was continued for 1 hours at 200° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing isophorone-isocyanate-methylurethane (monoisocyanate), isophorone dimethylurethane and IPDI. The mixing liquid was subjected to chromatography analysis. The measured IPDI had a purity of 87% and a IPDI chromatography yield of 85%. Then the mixing liquid was subjected to rectification. The isolated IPDI yield was 81%. The residual product after rectification was subjected to the next thermal cracking for circulation in turn. The ionic liquid could be reused for several times.

Example 19

In to a thermal cracking device, 500 mL of 1,2-dimethyl-3-butylimidazole tetrafluoroboric acid ionic liquid ([EMMIm]BF$_4$) and 0.8 g of supported metal oxide solid catalyst A were added. At 200° C., under an absolute pressure of 6500 Pa and a stirring rotation speed of 550 rounds/min, 235 g of 3-ethoxycarbonylaminomethyl-3,5,5-trim ethyl-1-ethoxycarbonylaminocyclohexane (isophorone diethylurethane) was further added. After reacting for 0.5 h, isophorone diisocyanate (IPDI) and ethanol were collected in the pre-(about 0° C.), post-(about −20° C.) collecting devices, respectively. The reaction was continued for 1 hours at 200° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing isophorone-isocyanate-ethylcarbamate (monoisocyanate), isophorone diethylurethane and IPDI. The mixing liquid was subjected to chromatography analysis. The measured IPDI had a purity of 94% and a IPDI chromatography yield of 90%. Then the mixing liquid was subjected to rectification. The isolated IPDI yield was 86%. The residual product after rectification was subjected to the next thermal cracking for circulation in turn. The ionic liquid could be reused for several times.

Example 20

In to a thermal cracking device, 500 mL of 1,2-dimethyl-3-butylimidazole perchlorate ionic liquid ([EMMIm]ClO$_4$) and 0.9 g of supported metal oxide solid catalyst E were added. At 200° C., under an absolute pressure of 6500 Pa and a stirring rotation speed of 500 rounds/min, 215 g of 3-butoxycarbonylaminomethyl-3,5,5-trimethyl-1-butoxycarbonylaminocyclohexane (isophorone dibutylurethane) was further added. After reacting for 0.5 h, isophorone diisocyanate (IPDI) and butanol were collected in the pre-(about 0° C.), post-(about −20° C.) collecting devices, respectively. The reaction was continued for 1 hours at 200° C. under a degree of vacuum of 6500 Pa. Then, the temperature was turned to 240° C. under the same degree of vacuum for 10 min. All of the products, raw materials and intermediates in the thermal cracking device were collected into the pre-collecting device to obtain a mixture containing isophorone-isocyanate-butyl-carbamate (monoisocyanate), isophorone diethylurethane and IPDI. The mixing liquid was subjected to chromatography analysis. The measured IPDI had a purity of 95% and an IPDI chromatography yield of 95%. Then the mixing liquid was subjected to rectification. The isolated IPDI yield was 93%. The residual product after rectification was subjected to the next thermal cracking for circulation in turn. The ionic liquid could be reused for several times.

Though the preferable examples in the invention are shown above, they are not used to limit this invention, and therefore, the protective scope of the invention should correspond to the scope of claims in the application patent.

What is claimed is:

1. A method for preparing isocyanates by liquid-phase thermal cracking, comprising:
    liquid-phase thermal cracking a reactant in the presence of a catalyst composition, the catalyst composition comprising a superfine powder metal oxide catalyst having a particle diameter of 0.5-10 micrometers and an ionic liquid, wherein:
    the reactant is an alkyl, an aryl dialkylurethane, or a multialkylurethane;
    the reactant is liquid-phase thermal cracked for a reaction time of 0.5-3 h under a reaction temperature of 160-220° C. and an absolute pressure of 1000-8000 Pa so as to prepare the corresponding isocyanate;
    the metal oxide catalyst comprises at least one selected from the group consisting of nickel oxide, titanium oxide, zirconium oxide, copper oxide, molybdenum oxide, iron oxide, tungsten oxide, lanthanum oxide, cerium oxide, cobalt oxide, zinc oxide, calcium oxide, yttrium oxide and bismuth oxide;
    the cation of the ionic liquid is represented by a structural formula selected from the group consisting of

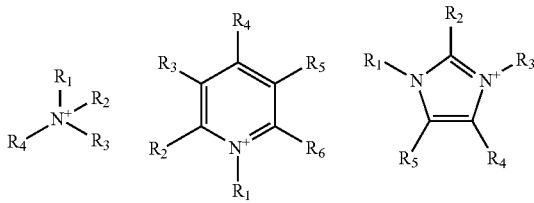

where $R_1$, $R_2$, $R_3$, $R_4$, $R_5$, $R_6$ each independently represents hydrogen or a branched or substituted alkyl group with a carbon number between 1 and 15; and
    an anion of the ionic liquid is selected from the group consisting of $NO_3^-$, $PF_6^-$, $HSO_4^-$, $ClO_4^-$, $CH_3PhSO_3^-$, $C(CN)_3^-$, $N(CN)_2^-$, $BF_2(CF_2)_nCF_3^-$ where n=0-10, $PF_3(CF_2)_nCF_3^-$ where n=0-10, $N(CF_3SO_2)_2^-$, $SCN^-$, $SeCN^-$, $RSO_3^-$ where R has carbon number of 0-10, $RSO_4^-$ where R has a carbon number of 0-10, $M_nY_x$ where M=Al, Zn, Fe, or Sn, X=Cl, Br, or I, n=1-2, x=2-7, $RCOO^-$ where R has a carbon number of 0-18, $BF_4^-$, $H_2PO_4^-$, $CF_3COO^-$, $CF_3SO_3^-$, $SbF_6^-$, $AsF_6^-$, $EtSO_4^-$, $MeSO_4^-$, $Cl^-$, $Br^-$ and $I^-$.

2. The method as claimed in claim 1, wherein the superfine powder metal oxide catalyst is a metal oxide or a composite of metal oxides.

3. The method as claimed in claim 2, wherein the metal oxide catalyst comprises at least one selected from the group consisting of zirconium oxide, molybdenum oxide, iron oxide, lanthanum oxide, cobalt oxide, zinc oxide, yttrium oxide and bismuth oxide.

4. The method as claimed in claim 1, wherein the metal oxide catalyst is a two component metal oxide catalyst comprised of two metal oxides A and B selected from the group consisting of nickel oxide, titanium oxide, zirconium oxide, copper oxide, molybdenum oxide, iron oxide, tungsten oxide, lanthanum oxide, cerium oxide, cobalt oxide, zinc oxide, calcium oxide, yttrium oxide and bismuth oxide.

5. The method as claimed in claim 4, wherein the mass ratio of metal oxide A to metal oxide B is 50:1-1:50.

6. The method as claimed in claim 1, wherein the metal oxide catalyst is a three component metal oxide catalyst comprised of three metal oxides A, B and C selected from the group consisting of nickel oxide, titanium oxide, zirconium oxide, copper oxide, molybdenum oxide, iron oxide, tungsten oxide, lanthanum oxide, cerium oxide, cobalt oxide, zinc oxide, calcium oxide, yttrium oxide and bismuth oxide.

7. The method as claimed in claim 6, wherein the metal oxide A comprises 10 wt % and the metal oxide B comprises 10 wt % based on the total weight of the metal oxide catalyst.

8. The method as claimed in claim 1, wherein an anion of the ionic liquid is one selected from the group consisting of $NO_3^-$, $PF_6^-$, $HSO_4^-$, $ClO_4^-$, $CH_3PhSO_3^-$, $C(CN)_3^-$, $BF_2(CF_2)_nCF_3^-$ where n=0-10, $PF_3(CF_2)_nCF_3^-$ where n=0-10, $N(CF_3SO_2)_2^-$, $BF_4^-$, $H_2PO_4^-$, $CF_3COO^-$, $CF_3SO_3^-$, $SbF_6^-$, $AsF_6^-$, $EtSO_4^-$, $MeSO_4^-$, $Cl^-$.

9. The method as claimed in claim 1, wherein the mass ratio of the superfine powder metal oxide solid catalyst to the ionic liquid is from 1:300 to 1:15000.

10. The method as claimed in claim 1, wherein the alkyl or aryl dialkylurethane is at least one selected from the group consisting of hexamethylene 1,6-dialkylurethane, dicyclohexylmethane-4,4'-dialkylurethane, isophorone dialkylurethane, p-cyclohexyldialkylurethane, diphenylmethane-4,4'-dialkylurethane, bis(2-tolyl)methane-4,4'-dialkylurethane, toluene-2,4-dialkylurethane, toluene-2,6-dialkylurethane, benzene-1,4-dialkylurethane and naphthalene-1,5-dialylurethane.

11. The method as claimed in claim 10, wherein the dialkyl- is dimethyl-, diethyl- or dibutyl-.

12. The method as claimed in claim 1, wherein the mass ratio of the alkyl or aryl dialkylurethane to the ionic liquid is 1:1-1:50.

* * * * *